United States Patent
Lubow

(10) Patent No.: US 7,389,928 B2
(45) Date of Patent: Jun. 24, 2008

(54) SYSTEM AND METHOD OF UTILIZING A MACHINE READABLE MEDICAL MARKING FOR MANAGING SURGICAL PROCEDURES

(75) Inventor: Allen Lubow, Brooklyn, NY (US)

(73) Assignee: International Barcode Corporation, New York, NY (US)

( * ) Notice: Subject to any disclaimer, the term of this patent is extended or adjusted under 35 U.S.C. 154(b) by 0 days.

(21) Appl. No.: 11/267,180

(22) Filed: Nov. 7, 2005

(65) Prior Publication Data

US 2006/0138211 A1 Jun. 29, 2006

Related U.S. Application Data

(60) Provisional application No. 60/626,834, filed on Nov. 10, 2004.

(51) Int. Cl.
*G06K 7/10* (2006.01)
(52) U.S. Cl. .............. 235/462.01; 235/462.08; 235/454; 235/462.15; 705/2; 705/3
(58) Field of Classification Search ............ 235/462.01, 235/462.08, 462.15, 454; 705/2, 3
See application file for complete search history.

(56) References Cited

U.S. PATENT DOCUMENTS

| 4,947,867 | A | 8/1990 | Keeton |
| 5,374,813 | A | 12/1994 | Shipp |
| 5,443,082 | A | 8/1995 | Mewburn |
| 5,795,312 | A | 8/1998 | Dye |
| 6,155,263 | A | 12/2000 | Weaver |
| 6,579,252 | B2 | 6/2003 | Lloyd et al. |
| 7,142,118 | B2 | 11/2006 | Hamilton et al. |
| 2004/0026501 | A1* | 2/2004 | Walsh .................... 235/380 |
| 2004/0082918 | A1* | 4/2004 | Evans et al. ............. 604/207 |
| 2004/0190780 | A1* | 9/2004 | Shiibashi et al. ......... 382/210 |
| 2005/0215901 | A1* | 9/2005 | Anderson et al. ........ 600/445 |
| 2006/0131391 | A1* | 6/2006 | Penuela ................. 235/380 |

FOREIGN PATENT DOCUMENTS

JP 2002119520 A * 4/2002

OTHER PUBLICATIONS

International Search Report and Written Opinion mailed Jan. 10, 2007 in corresponding International Application No. PCT/US2005/040732.

* cited by examiner

*Primary Examiner*—Michael G. Lee
*Assistant Examiner*—Kristy A. Haupt
(74) *Attorney, Agent, or Firm*—Davidson Berquist Jackson & Gowdey LLP

(57) ABSTRACT

The method and system include marking a surgery site (e.g., location of surgical incision) or a site of other medical action with a machine-readable medical marking (e.g., bar code or a dot pattern), which may be used in conjunction with (1) a scanner for reading the machine-readable medical marking and (2) a controller for controlling medical actions in response to the read machine-readable medical marking. The system and method ensure the validation of the surgical procedure, the patient awaiting the surgical procedure, and the site or location on the patient where the surgery is to be performed. Utilizing a scanning device for reading machine-readable medical markings, and a controller, there are additional means to check and double check the medical action before the actual medical action (e.g., surgery) is performed.

21 Claims, 8 Drawing Sheets

| Surgical Scheduler | |
|---|---|
| Patient Name: | John L. Lewis |
| Patient Code: | B341536K |
| Age: | 65 |
| Sex: | M |
| Surgical Procedure: | Knee Replacement |
| Side: | Left |
| Blood Type: | A- |
| Allergy(s): | NONE |
| Surgical Procedure Code: | IDC 31256 |
| Surgical Kit: | K45 |
| Prosthetic Devices: | KNEE |
| Xrays: | 35,46,57 |
| Charts: | 784524 |
| MRI/CAT/Other: | PAC 345146 |
| Lab Tests: | GL/PR 435 |
| Surgical Bar Code Number: | 16,437 |
| Operating Room: | 4R |
| Date: | October 14, 2004 |
| Start Time: | 16:00 |
| Expected Duration: | 4 hours |
| Staff: | ORN, PN, AN, AN2 |
| Comments: | Check blood pressure immediately before anesth. |
| Attending Physician: | Dr. Neil Young |
| Resident: | Dr. Cornell Weil |

(Surgical Bar Code: 16,437 shown in upper right)

Fig. 2

Bar code represents 512+128+1 = 641

SYSTEM AND METHOD OF UTILIZING A MACHINE READABLE MEDICAL MARKING FOR MANAGING SURGICAL PROCEDURES

CROSS-REFERENCE TO CO-PENDING APPLICATIONS

The present application is related to claims priority to U.S. Provisional Patent Application Ser. No. 60/626,834, filed Nov. 10, 2004. The entire contents of that application are incorporated herein by reference.

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND OF THE INVENTION

1. Field of the Invention

The present invention relates generally to a system and method for using a machine-readable medical marking for managing medical actions or procedures, and more particularly, to generating and using machine-readable medical markings that are used for accessing up-to-date data associated with a patient's medical information (e.g., pre-operative and post-operative information as well as information on the surgical procedure itself).

2. Discussion of the Background

During known surgical procedures, it is possible for mistakes to be made because a doctor incorrectly identifies any one of (1) a patient, (2) a procedure to be performed, (3) allergies of the patient, (4) site of the surgery, (5) level of the surgery, (6) diagnostic reports (e.g., lab reports for test results, blood results, etc.). Such a mistake may occur because there is an insufficient connection between (1) the patient (who may be unconscious), (2) the patient's information, and (3) the information about the patient's procedure. Accordingly, a need exists for providing a greater connection between (1) the patient (who may be unconscious), (2) the patient's information, and (3) the information about the patient's procedure.

SUMMARY OF THE INVENTION

According to an embodiment of the present invention, a method is provided for verifying information associated with a medical action (e.g., a surgical event or an administration of a medication) using a scanner device and at least one machine-readable medical marking applied to a patient (e.g., on the skin in close proximity to the surgical site or near where medication is to be administered). The information is verified prior to performing the medical action associated with the person.

The exemplary method comprises reading, using a scanner device, a machine-readable medical marking that is applied to the person, whereby patient information is accessed (e.g., by the scanner or a separate controller). The patient information is then compared with recorded information associated with the patient to verify that the correct action is about to be taken (e.g. "Is this the right patient?", "Is the right surgery about to be performed?", "Is the correct location about to be cut?", "Is a medicine about to be injected/administered that the patient is allergic to?"). Such a method may be performed by any one or a combination of: medical personnel during pre-operative procedures, medical personnel during surgical procedures, medical personnel during post-operative procedures, and medical personnel prior to administering medications. As used herein, "medical personnel" shall be understood to include surgical team members, pre-operative team members, post-operative team members as well as hospital doctors, nurses, nurses' aides, and generally anyone that administers medicine or medical procedures to a patient.

According to another embodiment of the present invention, the patient's medical information is displayed to one or more medical personnel. The medical information may include, but is not limited to, patient identity information (e.g., patient name, code, age, etc.), type of surgical procedure to be performed, required surgical equipment or kits, equipment set-up, medical history, allergies, surgical area, patient medical test information (e.g., x-rays, charts, MRI, lab tests), administrative resource information (e.g., staff and/or physician names, duration of procedure, operating room identifier), and/or surgical procedure information (e.g., procedure, blood type, surgical kit, etc.).

According to another embodiment of the present invention, verifying the one or more characteristics of the medical action may include comparing the accessed medication information with one or more of (1) machine-readable medical information associated with the medical action (e.g., barcoded x-rays, barcoded test results, barcoded wristbands on the patient, etc.), (2) visual indicators (e.g., the operating room number, the type of equipment present for the medical action, etc.), and (3) records associated with the patient (e.g., medical charts or electronic medical history).

According to another embodiment of the present invention, a method is provided, using a scanner device, for verifying one or more characteristics of a medical action prior to the occurrence of the action. The method comprises reading, using the scanner device, a machine readable medical marking applied to the patient receiving a medical action for accessing the information associated with the patient. A pre-event check is then conducted prior to the occurrence of the medical action, whereby the pre-event check comprises verifying that the characteristics of the action correspond to the accessed information before commencing the medical action.

According to another embodiment of the present invention, the medical status information is accessed by a surgical scheduling program.

According to another embodiment, additional medical information that may be verified includes, but is not limited to, information obtained from visual checks of the operating room.

According to another embodiment of the present invention, the machine-readable medical marking comprises a first encoded region and one or more other identical encoded regions that are readable by the bar code scanner when the first encoded region becomes unreadable.

According to another embodiment of the present invention, a method of utilizing a medical marking (e.g., a bar code) having a plurality of regions each comprising a machine-readable medical sub-marking for managing a medical action associated with one or more individuals is provided. The method comprises providing at least one machine-readable marking each having encoded thereon information (e.g., a unique record number) associated with at least one individual's medical action information, wherein at least one such machine-readable medical marking is applied to the individual's body (e.g., as a decal, tattoo or other semi-permanent marking). The patient's information records are encoded with corresponding information such that the at least one machine-readable medical marking and the patient's information can be compared and verified.

According to another embodiment of the present invention, a surgical operating room contains a first copy of the at least one machine-readable medical marking so that the medical action can be verified prior to surgery.

According to another embodiment of the present invention, the patient's medical charts also include a second copy of the at least one machine-readable medical marking so that the medical action can be verified prior to surgery.

According to another embodiment of the present invention, at least one medical personnel member accesses the patient's surgical information using the machine-readable medical marking applied to the patient and at least one of the first and second copies.

According to another embodiment of the present invention, a display device is provided for displaying the generated medical status information on the display device.

According to another embodiment of the present invention, a machine-readable medical marking comprises a plurality of cell regions organized into a plurality of encoding regions such that the plurality of encoding regions are spatially distributed. The plurality of encoding regions provide an indication of whether the machine readable medical marking has become corrupted.

According to another embodiment of the present invention, the plurality of encoding regions comprise redundant encoded regions.

According to another embodiment of the present invention, an orientation indicator located circumferentially to the plurality of cell regions is provided, where the orientation indicator provides orientation information associated with decoding each of the spatially distributed plurality of encoding regions.

According to another embodiment of the present invention, the plurality of encoding regions generates a numerical code that is encoded using a modulo-n based number system (e.g., a modulo-2 based number system).

According to another embodiment of the present invention, the plurality of spatially distributed encoding regions comprises at least two encoding regions that each generate an identical code. A difference between each generated code associated with each one of the two encoding regions determines the existence of one or more corrupted regions associated with the machine-readable medical marking.

According to another embodiment of the present invention, a machine-readable medical marking comprising a plurality of cell regions is organized into a plurality of encoding regions. The plurality of encoding regions are spatially distributed and comprise at least two encoding regions each generating an identical code. The difference between each generated code associated with each one of the two encoding regions determines the existence of one or more corrupted regions associated with the machine-readable medical marking.

According to another embodiment of the present invention, each of the machine readable medical markings may also include error detection and/or correction information to further increase the resilience of the symbols to error.

BRIEF DESCRIPTION OF THE DRAWINGS

For a more complete understanding of the present invention, and the advantages thereof, reference is now made to the following descriptions taken in conjunction with the accompanying drawings, in which

FIG. 2 is an illustration of an exemplary screenshot of a hypothetical medical scheduling system which includes patient information and its associated bar code information;

DETAILED DESCRIPTION OF THE PREFERRED EMBODIMENTS

Dramatic consequences can occur when a surgical procedure is performed on the wrong site or surgery location (e.g., left side instead of right side), on the wrong patient, or involves the wrong procedure. Thus, the method (and system) of the present invention includes marking a surgery site (e.g., location of surgical incision) or a site of other medical action with a machine-readable medical marking (e.g., bar code or a dot pattern), which may be used in conjunction with a scanner for reading the machine-readable medical marking and a controller for controlling medical actions in response to the read machine-readable medical marking. The system and method of the present invention ensures the validation of the surgical procedure, the patient awaiting the surgical procedure, and the site or location on the patient where the surgery is to be performed. A protocol may also be established which makes the scanning or reading of the machine-readable medical marking an integral part of the surgical method. Through the use of this protocol, a scanning device for reading machine-readable medical marking, and a computer system, there are additional means to check and double check the medical action before the actual medical action (e.g., surgery) is performed.

The protocol and system described herein facilitates the performance of certain checks, and establishes a verifiable path to decisions about the patient, the surgical site on the patient, and the surgical procedures. Thus, the medical personnel are guided to correct information associated with the patient and the corresponding surgical procedure. The system and method described herein, therefore, generally relate to the field of health care, and may be used to warn and prevent health care providers from inadvertently performing a medical action on the wrong site, the wrong patient, or with the wrong procedure. The system and method described herein may be employed in, but is not limited to, hospitals, acute care centers, emergency rooms, doctor's offices, nursing homes, convalescent hospitals, field hospitals, and all other medical and health-care facilities were surgical procedures may be performed.

Figure 1:
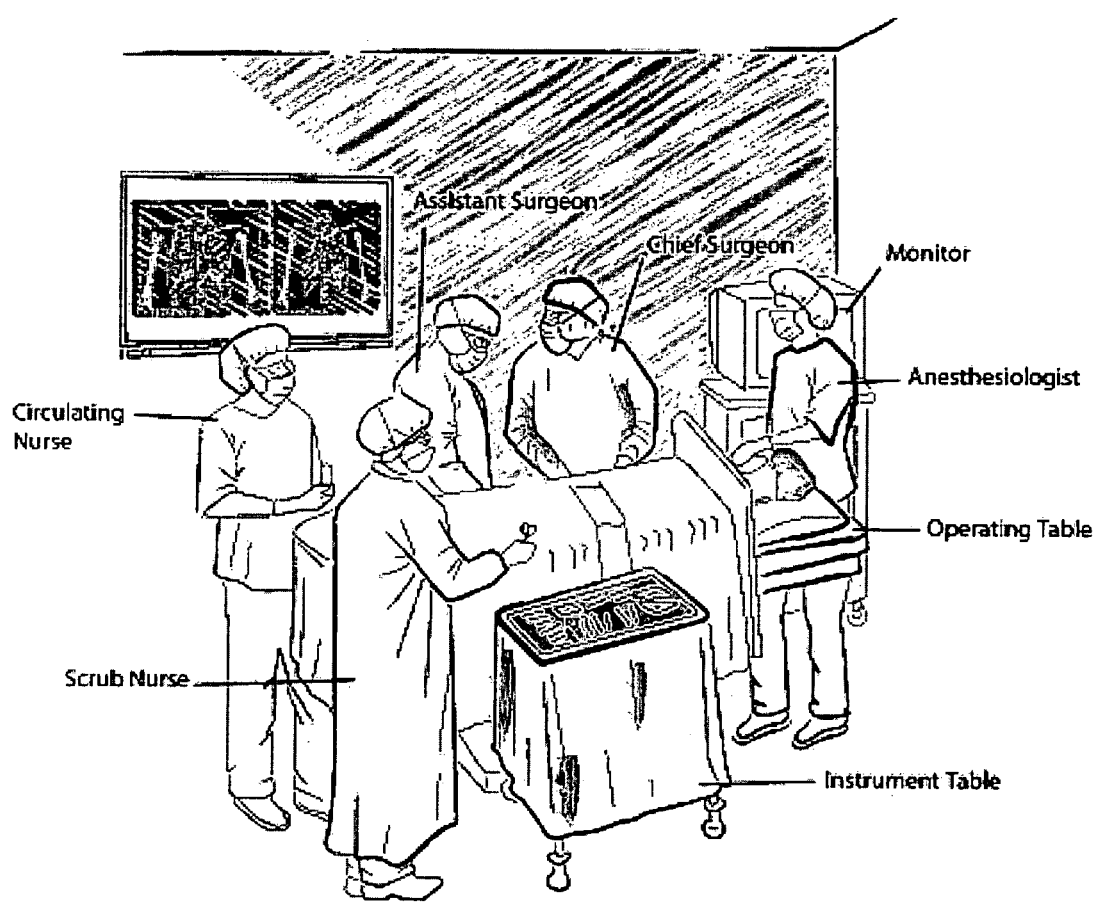
FIG. 1 is an illustration of an exemplary environment in which the present invention can be utilized.

FIG. 1 illustrates a medical operating room in which the present invention can illustratively be utilized. In FIG. 1, the patient on which surgery is to be performed has been pre-marked with a machine readable medical marking. In addition, based on the medical marking read from the patient, information about the patient can be recalled on the monitor to ensure that the surgeon is performing the correct procedure. Similarly, the anesthesiologist can confirm from the monitor that the anesthetic that is about to be administered is correct. Likewise, the surgeon can verify that the patient and the x-rays being inspected are encoded with the same information (e.g., patient identifier or patient record identifier).

The system according to an embodiment of the present invention comprises a scheduler computer program, a computer or display device in the Operating Room (OR), and a scanner device for reading the machine-readable medical marking, which is also present in the OR. The scheduler program can be a "Surgical Scheduler" program as illustrated in FIG. 2, which produces or correlates a machine-readable medical marking (which is applied to the surgical site or other medical action site) with other patient and medical information. As shown in FIG. 2, the scheduler information may include the surgical procedure, the location, the blood type of the patient and all the other information illustrated on FIG. 2. As such, prior to performing a medical action, the medical personnel may scan the medical marking and access the information corresponding to the patient by calling up the record (illustrated as record 16,437) corresponding to the number (or other information) read from the medical marking.

Thus, the surgical scheduler program allows medical personnel to enter pertinent information about the patient and the associated procedure to be performed. It may also provide an opportunity to enter vital information for the successful outcome of the surgery including, but not limited to, a patient's medical records, lab tests, x-rays, charts, required prosthetic devices, required surgical kits, staffing requirements, date and time, etc. In a hospital or other healthcare facility where several operating rooms are used simultaneously, the scheduler program may also allow entry of the determined time and place of the surgical procedure in addition to entered information, materials, and staff requirement assignments (e.g., needed presence of anesthetist).

In the operating room during the "time-out" phase, the surgeon may be required to use a machine-readable medical marking scanner for reading the information from the patient's machine-readable medical marking. The scanned information (e.g., number) is then fed into the "Scheduling Software" running on a computer, whereby the patient's record is displayed on a monitor device in the operating room based on the scanned number. The surgical team's "time-out" would include a review of this record, which includes a list of requirements for the procedure including, but not limited to, patient name, procedure, surgical kits, test result information (e.g., x-rays), procedure code, and other requirements. Only after confirmation of such information would the operating room nurse hand the scalpel to the surgeon in order to commence surgery. The "Time-out" is generally performed immediately prior to starting the surgical procedure in order to prevent medical error by conducting a final verification of the correct patient, procedure, and site. This provides active (two-way) communication among all surgical/procedural team members prior to all procedures.

Additionally, the scheduling program may be extended to act as a "controller" and provide active monitoring of medical sub-actions during a medical action. For example, by encoding the type and order that medical devices are to be used in, and by actively monitoring the use of the medical devices, other mistakes may be avoided. An exemplary use of active monitoring is described below.

In an exemplary use of the present invention, when a patient is admitted, the machine-readable medical marking is associated with the patient's physical chart and electronic surgery schedule, preferably by scanning a decal that is affixed to or printed on the patient's physical chart. Then, the patient's blood type and a list of known allergies are recorded using computer readable codes (e.g., blood type O-negative is encoded with a $blood_1$ code, and an allergy to $anesthetic_1$ is encoded with a $code_1$). Moreover, the fact that a patient is to have a hip replacement that is designed to last 15 years instead of 10 years is encoded by recording the part number of the hip replacement to be used in the replacement. The location of where the medical action is to be performed is then associated with the patient's records as well.

After recording the information during or prior to patient intake, the patient is taken to have the machine readable medical marking applied to his or her skin in an area surrounding or in close proximity to where the medical action (i.e., hip replacement surgery in the example) is to be performed. Later, the patient is taken to where the medical action is to be performed. Before entering, the medical marking and the machine readable location code on the door or doorframe of the room are both scanned. The enhanced scheduler then notifies the orderly if the patient is about to be brought into the correct location.

Similarly, prior to inserting the anesthetic in the dispenser, the anesthesiologist scans the medical marking on the patient and then a machine readable drug marking on the anesthetic. If there is a conflict with a previously entered allergy as signified by the machine readable drug marking matching $code_1$ for anesthetic, then the anesthesiologist is warned about the mismatch. Alternatively, in an embodiment where the scheduler is connected to the dispenser, the dispenser can be commanded to prevent the $anesthetic_1$ from being dispensed.

In another phase of the medical procedure, the surgeon utilizes a scanner to scan the bar code or other machine readable marking on the replacement part. In such a case, the scheduler can actively inform the surgeon that he has been brought a 10-year hip replacement part instead of the intended 15-year hip replacement part—a difference that medical personnel might not be able to tell by visual inspection.

In another exemplary embodiment, all blood used in a transfusions or in surgery is marked with a machine readable marking. Thus, prior to administering the blood, the blood bag and the patient's medical marking are scanned to assure that there is a match or at least that they are compatible. As with all checks, the scheduler can inform medical personnel of agreement (e.g., with a first audible tone, sound or visual indication) or conflict (e.g., with a second audible tone, sound or visual indication). In a case of the scheduler being integrated to a blood pump, the scheduler could also refuse to pump if there is a disagreement between the markings.

In one embodiment, all of the collateral information that the system would require as part of the surgical procedure such as x-rays would be marked with the same number encoded in a machine-readable medical marking. A check could be made by scanning the machine-readable medical marking on the collateral information as a double check that the x-rays are the correct ones for this particular surgery. As part of the methodology, therefore, the labels with the machine-readable medical marking would have to be affixed to the x-rays, lab tests, and other pertinent medical test records etc. Alternatively, numbers may be assigned to each x-ray, as well as to any other collateral material associated with the patient and the surgical procedure.

The information that is displayed on the screen in the Surgical Scheduler is indicative of the information gathered prior to the surgery during the scheduling process and is also displayed in the Operating Room. An advantage of the system would be that information could be changed up to and including during the operation so that the latest and more up-to-date information is always available to those who depend on it. The scanner for reading the machine-readable medical marking provides machine-readable medical marking readability under the difficult conditions of having the images printed on the skin. The scanner would use the read bar code number to access a patient's record stored by the "Surgical Scheduling" software program. The patient's record may be stored in a local or remote database, or in any other local or remote storage medium. The accessed record may then be displayed on the screen in the Operating Room. Some verifiers or indicators may be used when a record of a cancelled or completed surgery is found. For example, a "Stop" sign would be displayed if a surgery is cancelled.

As described above, in one embodiment, an entry for each surgical procedure on a patient is designated by a number. In such an embodiment, medical markings each comprise a number (e.g., preprinted on a surgical decal) that is assigned to a patient's procedure. The particular requirements of a machine-readable medical marking may comprise the ability to encode a sufficient range of numbers (e.g., 1 to 99,999); the ability to be printed on an unreliable surface such as a patient's skin; the ability to be readable even when it has been partially obliterated by washing, application of bandages, and/or other interventions; and the ability to have redundancy of information and ways of self-checking.

Figure 4:
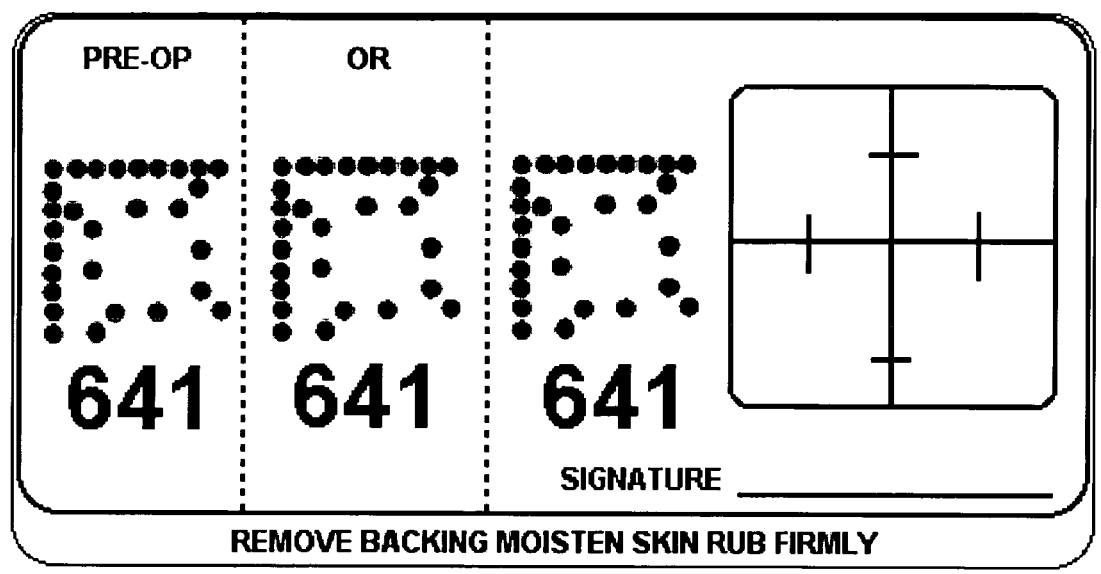
FIG. 4 is an illustration of a multi-part decal including plural copies of a medical marking to be used according to the present invention.

In an exemplary embodiment illustrated in FIG. 4, a decal has three copies of the number printed in the form of a machine-readable medical marking (e.g., bar code) and human-readable form. The first copy of the number (first part of decal) is a barcode which may be applied to a patient's physical medical chart. The second copy (second part of decal) of the number may be removed and maintained by an operating room nurse or a person in charge of operating room administration for the purpose setting-up the operating room facilities and resources prior to surgery. In the pre-operative visit, the surgeon may take the third part of surgical decal (third copy of number) and apply it directly to the patient at the site at which the surgery is to be performed (i.e., on the skin of the surgical site), potentially utilizing cross hairs to mark the site on the patient where the surgical procedure is to be performed. In one embodiment, this section of the decal is applied to a patient by wetting and pressing it onto the patient's skin. The surgical decal may include a place for the surgeon to mark and/or sign (e.g., with a felt tip pen).

The surgical decal (e.g., the machine-readable medical marking, human-readable code, cross hairs, and signature line) may be created by preprinting a clear plastic substrate with an ink specially formulated to adhere to the plastic and then covering the printing with a backing. The ink may be removed easily and transferred to the patient's skin once applied. On the skin, the ink remains somewhat permanent; it will not wash off, smear or fade in less than, for example, ten days. Thus, the "tattooed" image on the patient's skin remains sharp and consistent. The ink color used may be dark (e.g., black) and may therefore be readable by the bar code scanner, even where contrast would be difficult on patients with skin of very dark color.

In use, the left-most machine-readable medical marking of FIG. 4 and human readable number would be separated from the decal and affixed to the patient chart when the number is assigned to the patient's surgical procedure, as described above with respect to the patient intake. In a pre-operative meeting, the surgeon would affix the machine-readable medical marking, cross hairs, and signature line to the patient's skin at the surgical site by removing the backing and applying the medical marking after having verified with a scanner that the medical marking applied to the patient's chart matches the medical marking being applied to the patient.

The number of the decal may be unique (e.g., within a large set). The decals supplied to a hospital may be in book format with numbers starting at one and going up to some large number before the series is completely used up. A very large facility having several operating rooms that are used simultaneously, may perform 100,000 operations per year. If each surgery includes a uniquely assigned number, a numbered series would be supplied to the hospital without repeating numbers for a very long time. Books of decal numbers from 1 to 100,000 may, for example, last about a year.

Alternatively, the medical marking may be more than just a number. For example, the medical marking may be an alphanumeric string (e.g., X0001).

In yet another embodiment, the medical marking may be applied using techniques other than decals. For example, the medical marking may be applied to the patient using a computer-controlled printing apparatus such as an ink-jet printer, a plotter or a tattooing machine. In addition, in one embodiment of the present invention, the topology of the site of the medical action is determined such that a modified bar code can be created that causes the printed bar code to appear linear despite being applied to a non-planar surface.

As an alternative to cross hairs, the medical marking may utilize other indicators (e.g., arrows) to indicate the intended surgical site.

Figure 3:
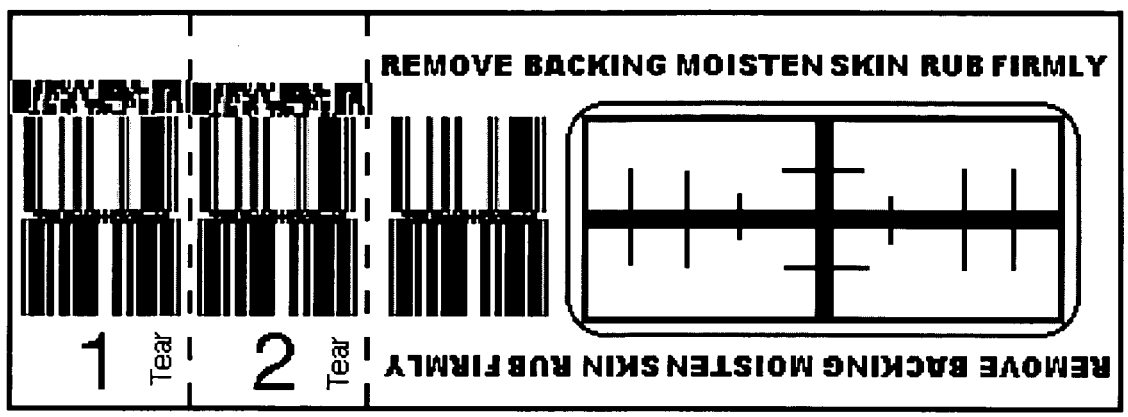
FIG. 3 is an illustration of a multi-part decal including plural copies of plural medical markings to be used according to the present invention where the plural medical markings can each carry different types of information.

The medical marking shown in FIG. 3 utilizes several traditional bar code formats, although it is possible to utilize only one. The illustrated formats include two linear formats and one reduced symbology format. These bar code formats enable the information (e.g., record number) to be associated with the patient to be semi-permanently affixed to the patient. In the example of FIG. 3, a portion of the machine-readable medical marking comprises a RSS bar code symbol that holds considerably more information than the other bar code portions. Therefore, it may be possible to include a sufficient amount of information in the bar code itself that the scheduling system need not be consulted during the medical procedure.

As an alternative to the format illustrated in FIG. 3, FIG. 4 illustrates a computer-readable marking printed as a decal and utilizing redundant coding. The medical marking of FIG. 4 is encoded using the encoding technique of FIG. 5A.

Figure 5A:
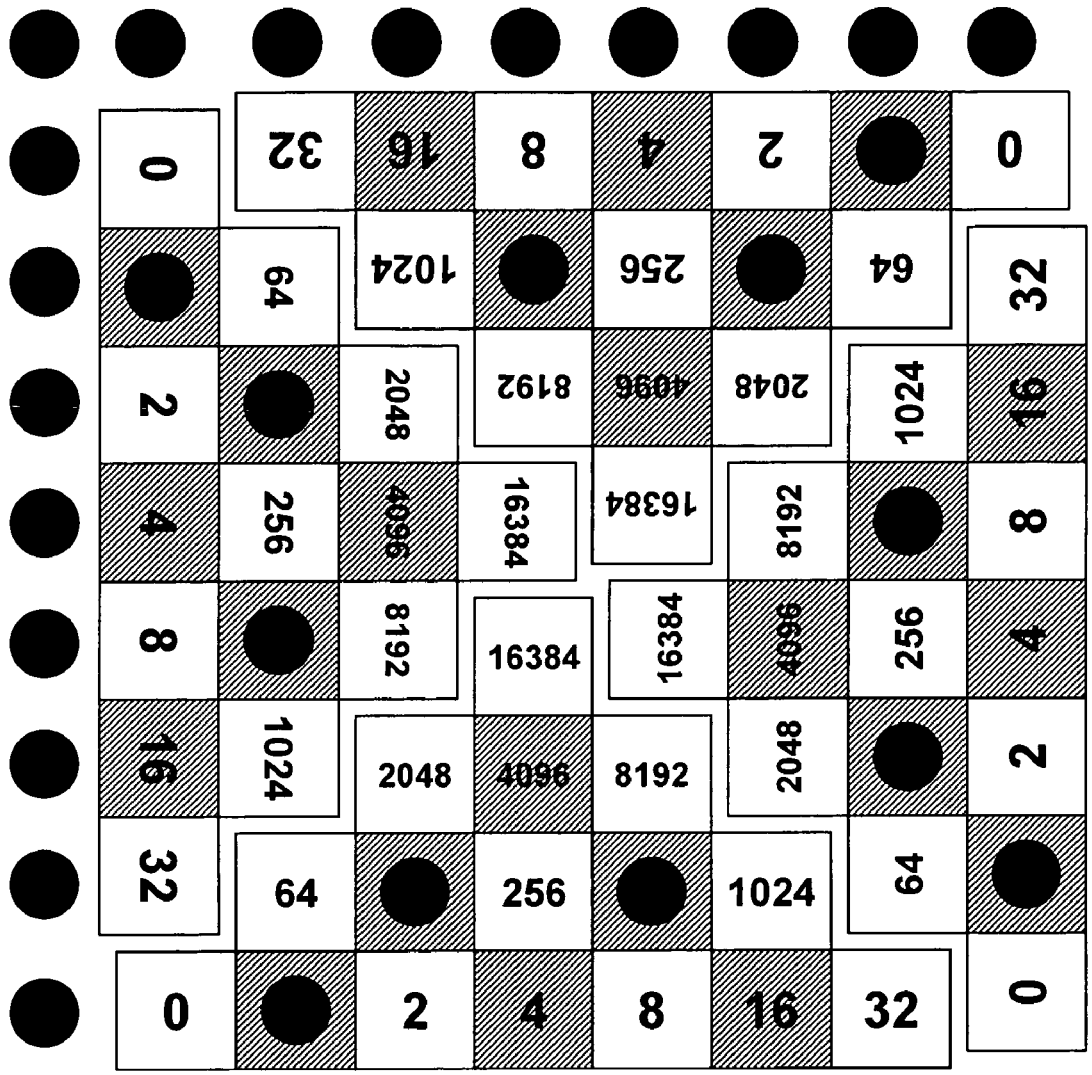
FIG. 5A is an illustration showing a medical marking utilizing a first encoding scheme providing four-way redundancy.

The medical marking of FIG. 5A comprises a pattern of colored dots (e.g., black) in a gridded fashion. In the illustrated embodiment, the bar code, called a "Surgical Bar Code" has four-way redundancy. As illustrated in FIG. 5A, the checkerboard grid is divided into four identical regions each having the same pattern of colored dots. The numbering system is based on the base-2 system. For example, in the provided pattern, a colored dot is placed at the "128" position (i.e., $2^7$), "512" position (i.e., $2^9$), and the "1" position (i.e., $2^0$). This produces the number 641 (i.e., 512+128+1), which is generated from the sum of numbers associated with the position of the colored dots. The pattern is repeated four times so that if one or more portions of the bar code is obliterated, covered, or removed, the remaining region or regions of the bar code are still readable. The inverted 'L' shaped border of black dots provides the scanner with the x-dimension information and orientation information. The decoding algorithm will determine the x-dimension, orientation, and the number (e.g., 641) corresponding to the colored dots allocated within the grid.

Figure 6:
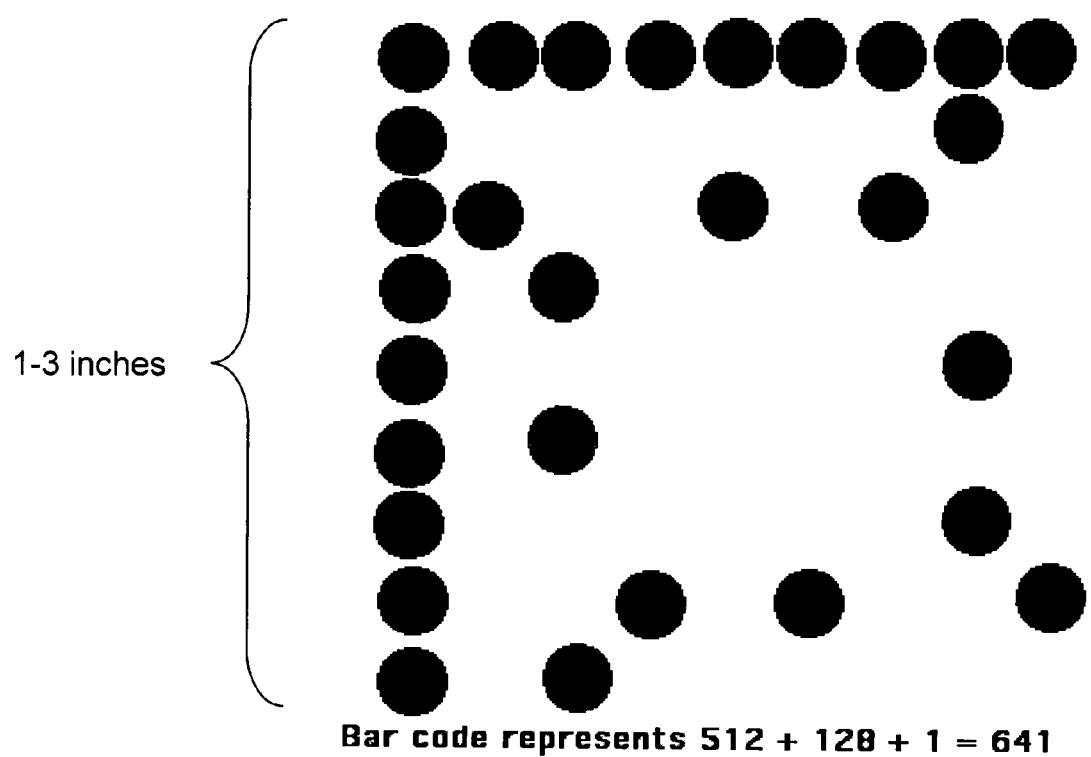
FIG. 6 is an illustration showing a medical marking utilizing four-way redundancy which encodes a value of 641.

FIG. 6 illustrates the example of encoding using the numbering scheme of FIG. 5A but without the corresponding numbers underneath and therefore resembles the medical marking as it is used in FIG. 4. The side length (as a square) or diameter (as a dot) of the cell is variable in size and is illustrated as being 1 to 3 inches on a side.

For small and hard to see or reach areas, the decal and machine-readable medical marking can be printed at various sizes. For example, the same imagery may be printed at half-size for images required for hands or fingers.

Figure 5B:
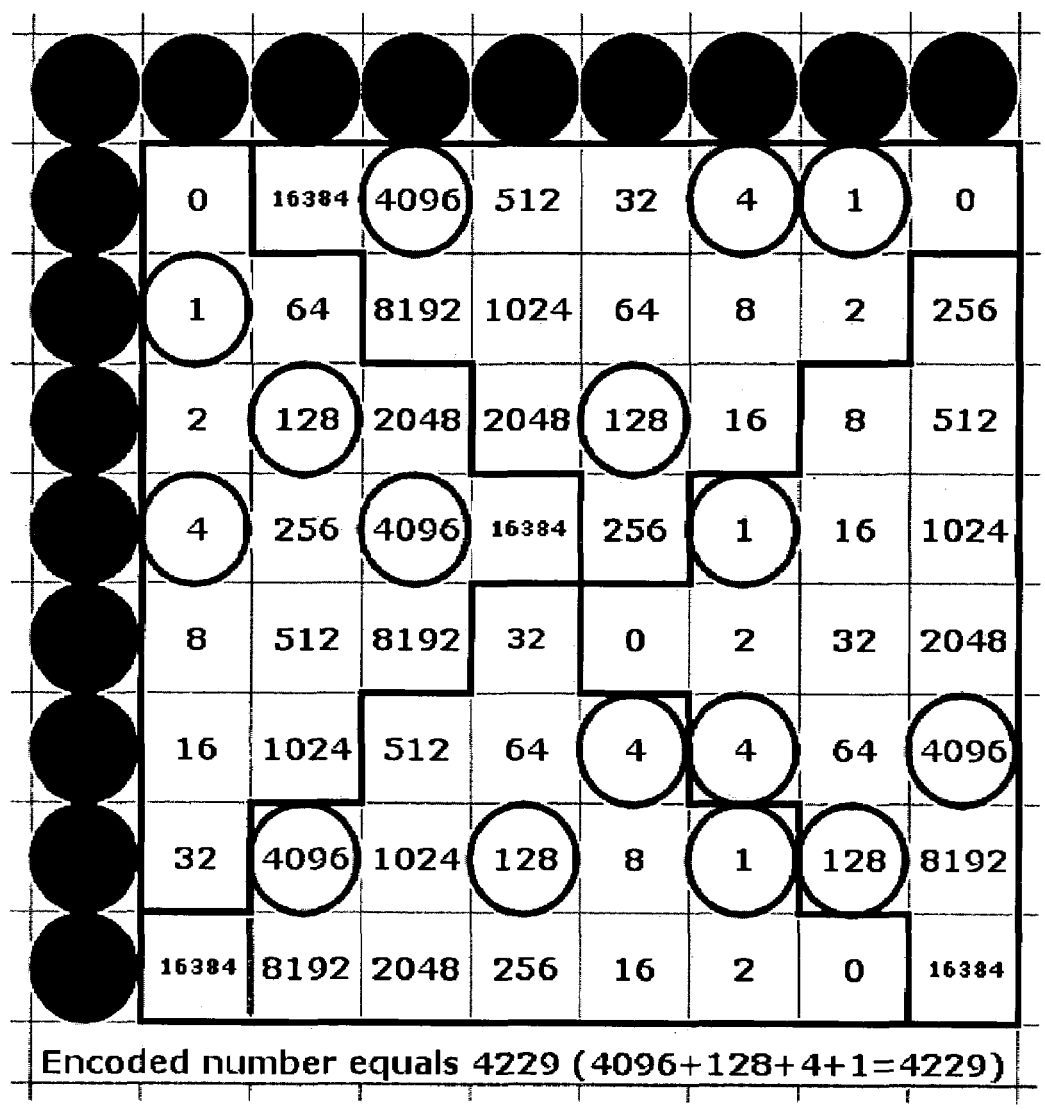
FIG. 5B is an illustration showing a medical marking utilizing a second encoding scheme providing four-way redundancy.

Alternatively, instead of having symmetric encoding as in FIG. 5A, the encoding of FIG. 5B distributes the locations of the values such that a smudge or other obstruction in the center of the medical marking will not obliterate all the locations having the same value (e.g., 16384).

Figure 7:
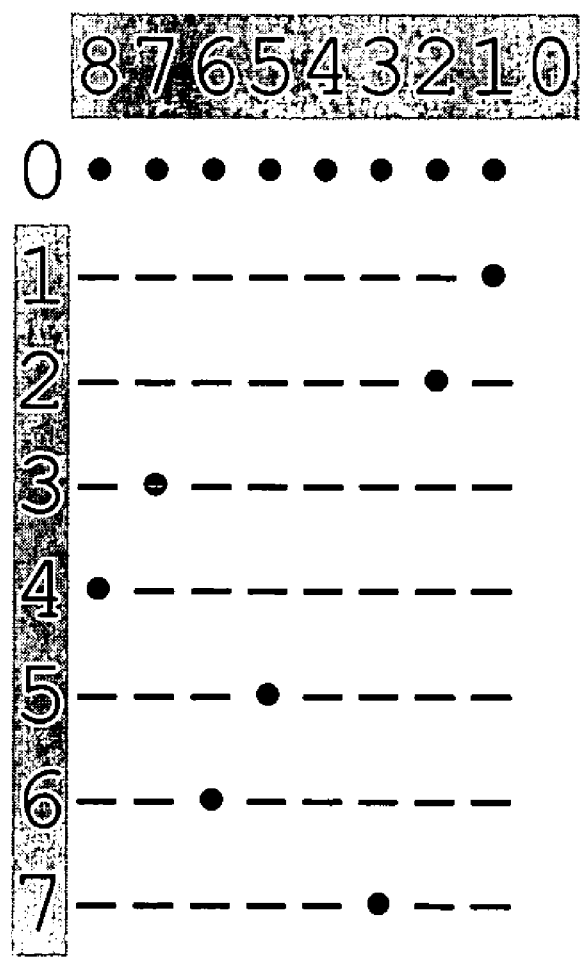
FIG. 7 is an illustration showing an alternate medical marking format.

According to yet another embodiment of the present invention, a "Checkerboard" machine-readable medical marking, such as is illustrated in FIG. 7, can encode a numeric string (e.g., a positive number). The Checkerboard machine-readable medical marking provides, among other things, a machine-readable medical marking having a size that is relatively small; similar measurements in different directions (e.g., substantially square shaped); and internal dimensions that are relatively large, which allows for the provision of a high numerical range.

Such a machine-readable medical marking may be readable when it is applied to some small area with a rough surface such as somewhere on a person's body. A "Checkerboard" symbol may comprise one or more "cells" (e.g., a square or spot) that is the smallest component of a Checkerboard machine-readable medical marking. A cell is printable if ink is applied to it with some foreground ink. When a spot or other indicator is marked (e.g., ink) within a cell, it is defined as a printable cell, since the spot or indicator may be applied or tattooed to the patient or person's skin. A printable cell is unprinted if it is left blank or printed with some background ink. Since a blank cell (e.g., unprinted cell) does not have a spot or indicator, it may not be applied or tattooed to the patient or person's skin; therefore, it is defined as an unprinted cell. A "row" or "column" is a series of cells arranged next to each other.

A Checkerboard machine-readable medical marking (e.g., bar code) such as that illustrated in FIG. 7 may comprise a (2N+1) row by 2N column rectangle, which is almost a square. In the example Checkerboard machine-readable medical marking, the rows start from the topmost position, which is row 0, and the columns start from the rightmost position, which is column 0. All printed cells in row 0 are called the "orientation bar." A row with an odd position is a "coding row." A row with an even position, except for row 0, is a complement-coding row, which is used to provide an identical and redundant code to that generated by the "coding row." In the event that a "coding row" becomes corrupted or unreadable, the complementary code row is used in its place to determine or decode the value associated with bar code symbol.

In a coding row, all cells at an even position (column) are printable whereby each printed cell has a value of:

$$2N[(i-1)/2]+(j/2)$$ Equation 1

If printed, a black dot or other indicia may be allocated to represent a cell position. If nothing is printed at a cell location (e.g., no black dot present in cell position), then the cell value at that position is assumed to be zero.

In Equation 1, "i" is the position of the row, "j" is the position of the column, and "N" is the order of the symbol. For the "coding row," the position of the first column (i.e., j=0) starts under heading "1," where the column headings are located above row i=0 and labeled "8 7 6 5 4 3 2 1 0."

In a "complement coding row," all cells at an odd position (column) are printable and each cell has a value of:

$$2N[(i-2)/2]+(j-1)/2$$ Equation 2

For a printed cell, a black dot or other indicia may represent a cell position. If nothing is printed at a cell location (e.g., no black dot present in cell position), then the cell value at that position is assumed to be zero.

In Equation 2, "i" is the position of the row, "j" is the position of the column, and "N" the order of the symbol. For the "complement coding row," the position of the first column (i.e., j=0) also starts at heading "1," where, as previously described, the column headings are located above row i=0. The sum of all values from all cells positions in all "coding rows" is the value of the symbol. Also, the sum of all values from all cells in all "complement coding rows" corresponds to the value of the symbol. When the bar code symbol has not become corrupted or defaced, the calculated values based on the "coding rows" and "complement coding rows" should be identical. In use, upon scanning the bar code, an error is detected if the two values calculated from the "complement coding rows" and "coding rows" are different.

The Checkerboard bar code symbol of FIG. 7 utilizes a value of N which is 4. This indicates that the symbol is 4-ordered. Row i=0 is the orientation bar; rows 1, 3, 5, and 7 are the "coding rows;" and rows 2, 4, 6, and 8 are the "complement coding rows."

As illustrated in FIG. 7, the first printed cell at i=1 and j=0 (starting at column heading 1) is a "coding row." Therefore, based on Equation 1, the value is 4[(1−1)/2]+(0/2)=0. For the second printed cell associated with a coding row, where i=3 and j=6, the value is 4[(3−1)/2]+(6/2)=7. Similarly, for the third "code row" printed cell, where i=5 and j=4, the value is 4[(5−1)/2]+(4/2)=10. The fourth "code row" printed cell, whereby i=7 and j=2 is calculated to be 4[(7−1)/2]+(2/2)=13. Therefore, based on the foregoing individual calculations, the value of the symbol is calculated from the sum of each cell value, which is:

$$2^{0 \ (for \ i=1)}+2^{7 \ (for \ i=3)}+2^{10 \ (for \ i=5)}+2^{13 \ (for \ i=7)}=1+128+1024+8192=9345$$

Based on the "complement coding rows," the first printed cell is located at i=2 and j=1. Thus, using Equation 2, the value for this cell (i=2 and j=1) is calculated to be 0. For the second printed cell located at i=4 and j=7, the value is 4[(4−2)/2]+(7−1)/2=7. For the third printed cell at i=6 and j=5, the value is 4[(6−2)/2]+(5−1)/2=10. For the fourth printed cell at i=8 and j=3, we have 4[(8−2)/2]+(3−1)/2=13. Therefore, the value of the symbol based on the "complement coding row" printed cell values is:

$$2^0+2^7+2^{10}+2^{13}=1+128+1024+8192=9345$$

As shown in the example, both cell values (i.e., code row and complementary row) generate identical symbol values when the integrity of the bar code symbol is intact. Each row includes a spatially adjacent redundant row having complementary cells. The complementary cells are both horizontally and vertically displaced from their "code row" counterpart cells located in adjacent rows. Therefore, the horizontal and vertical displacement provides spatial redundancy associated with rows that are damaged and unreadable.

In one embodiment of the invention, the scanner device described above is connected to a computer in the operating room. The connection may be either wired or wireless, depending on the configuration of the room in which the device is to be used. Moreover, the device may be a wand-style scanner, a gun-style scanner, a flat-bed scanner or any other style scanner that reads bar codes.

The active monitoring of the medical action need not be performed by a computer. Instead, a separate device, such as a handheld scanner (optionally with a display) and an internal processor may act as an integrated scanner and controller. The information about the patients of the day and the medical actions to be performed thereon can be downloaded to the handheld scanner in the morning such that the medical personnel can act autonomously from any local or remote computer systems that might "crash" or become disconnected during the day. Thus, the medical marking applied to the patient and the medical markings associated with the medical action would be scanned sequentially (or in parallel) by the handheld scanner, and the handheld scanner would visually or audibly identify whether the patient and the procedure about to be performed were compatible. As described above, if the patient's medical marking is scanned and then a blood bag is scanned which contains blood that is incompatible with the patient, then the handheld scanner can sound a warning signal. Alternatively, the medical personnel can acts as controllers by comparing the information read by a scanner with information displayed or printed about the medical action to be performed. Furthermore, while the above description has been provided in terms of a barcode scanner reading a medical marking, the teachings of the present invention may additional be used in conjunction with other machine-readable medical tags carrying information. One example of such a machine-readable medical tag is an RFID tag such as may be embedded into a patient's wristband. Moreover, a combination of reading devices can be used such that the patient is identified by a machine-readable medical tag while the surgical equipment and test results are encoded with bar codes such that the reading devices communicate (either with each other or with a central controller) to ensure that the information read from each is consistent.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modifications are intended to be included within the scope of the invention. Except to the extent necessary or inherent in the processes themselves, no particular order to steps or stages of methods or processes described in this disclosure, including the Figures, is implied. In many cases the order of process steps may be varied without changing the purpose, effect or import of the methods described.

The invention claimed is:

1. A medical system, comprising:
    a machine-readable medical marking applied to the skin of a patient in proximity to where a surgical operation is to be performed;
    a scanner for scanning the machine-readable medical marking applied to the skin of the patient;
    a source of information about the surgical operation to be performed on the patient; and
    a controller for comparing that the machine readable medical marking applied to the patient is consistent with the surgical operation to be performed on the patient prior to performing the surgical operation,
    wherein the information contained within the source of information comprises at least one of: a list of instruments needed for the surgical operation, a list of surgical kits needed for the surgical operation, and a list of medical reports needed before commencing the surgical operation.

2. The medical system as claimed in claim 1, wherein the machine readable medical marking comprises a barcode.

3. The medical system as claimed in claim 1, wherein the source of information comprises a local database entry indexed by the information encoded by the machine-readable medical marking.

4. The medical system as claimed in claim 1, wherein the source of information comprises a remote database entry indexed by the information encoded by the machine-readable medical marking.

5. The medical system as claimed in claim 1, wherein the controller comprises a computer.

6. The medical system as claimed in claim 1, wherein the scanner and the controller are integrated into a handheld scanner.

7. The medical system as claimed in claim 1, wherein the controller disables a medical device if the machine readable medical marking applied to the patient is incompatible with the medical action to be performed on the patient.

8. A medical system comprising:
    a first machine-readable medical marking applied to the skin of a patient in proximity to where a medical action is to be performed;
    a source of information about the medical action to be performed on the patient, wherein the source of information comprises a second machine readable medical marking;
    a scanner for scanning the first machine-readable medical marking applied to the skin of the patient and the second machine readable acting as the source of information about the medical action to be performed; and
    a controller for comparing, prior to performing the medical action, that the first machine readable medical marking applied to the patient is consistent with the medical action to be performed on the patient based on the second machine readable medical marking.

9. The medical system as claimed in claim 4, wherein the second machine readable medical marking is affixed to a medical chart of the patient.

10. The system as claimed in claim 8, wherein the first and second machine readable medical markings comprise barcodes.

11. A medical action controlling method comprising:
    applying a machine-readable medical marking to the skin of a patient in proximity to where a surgical operation is to be performed;
    scanning the machine-readable medical marking applied to the skin of the patient using a scanner;
    accessing a source of information about the surgical operation to be performed on the patient;
    comparing that the machine readable medical marking applied to the patient is consistent with the surgical operation to be performed on the patient prior to performing the surgical operation; and indicating an incompatibility when the machine readable medical marking applied to the patient is inconsistent with the surgical operation to be performed on the patient, wherein the information contained within the source of information comprises at least one of: a list of instruments needed for the surgical operation, a list of surgical kits needed for the surgical operation and a list of medical reports needed before commencing the surgical operation.

12. The medical action controlling method as claimed in claim 11, wherein the machine readable medical marking comprises a barcode.

13. The medical action controlling method as claimed in claim 11, wherein accessing comprises accessing a local database entry indexed by the information encoded by the machine-readable medical marking.

14. The medical action controlling method as claimed in claim 11, wherein accessing comprises accessing a remote database entry indexed by the information encoded by the machine-readable medical marking.

15. The medical action controlling method as claimed in claim 11, wherein the controller comprises a computer.

16. The medical action controlling method as claimed in claim 11, wherein the scanner and the controller are integrated into a handheld scanner.

17. The medical action controlling method as claimed in claim 11, wherein the controller disables a medical device if the machine readable medical marking applied to the patient is incompatible with the medical action to be performed on the patient.

18. A medical action controlling method comprising:

applying a first machine-readable medical marking to the skin of a patient in proximity to where a medical action is to be performed;

converting a source of information about the medical action to be performed on the patient into a second machine readable medical marking;

scanning, using a scanner, the first machine-readable medical marking applied to the skin of the patient and the second machine readable medical marking acting as a source of information;

comparing, prior to performing medical action, that the first machine readable medical marking applied to the patient is consistent with the medical action to be performed on the patient based on the second machine readable medical marking; and indicating an incompatibility when the first machine readable medical marking applied to the patient is inconsistent with the medical action to be performed on the patient.

19. The medical action controlling method as claimed in claim 18, wherein the second machine readable medical marking is affixed to a medical chart of the patient.

20. The method as claimed in claim 18, wherein the first and second machine readable medical markings comprise barcodes.

21. A medical system, comprising:

a machine-readable medical tag affixed to a patient;

a scanner for scanning the machine-readable medical affixed to the patient;

a source of information about a medical action to be performed on the patient; and a controller for comparing that information read from the machine readable medical tag affixed to the patient is consistent with the medical action to be performed on the patient prior to performing the medical action, wherein the medical action comprises a surgical operation, and wherein the information contained within the source of information comprises at least one of: a list of instruments needed for the surgical operation, a list of surgical kits needed for the surgical operation, and a list of medical reports needed before commencing the surgical operation.

* * * * *